United States Patent
Bizzio

[19]

[11] Patent Number: 6,157,004
[45] Date of Patent: Dec. 5, 2000

[54] ELECTRIC HEATING OR PREHEATING FURNACE PARTICULARLY FOR LINING CYLINDERS AND/OR FOR FIRING METAL-CERAMIC

[75] Inventor: Nickolas Bizzio, Monte-Carlo, Monaco

[73] Assignee: Peacock Limited L.C., Cheyenne, Wyo.

[21] Appl. No.: 09/408,044

[22] Filed: Sep. 29, 1999

[51] Int. Cl.[7] .................................................. F27D 11/00
[52] U.S. Cl. ........................... 219/390; 373/109; 219/420
[58] Field of Search ................................... 373/109, 110, 373/111, 112, 117, 118, 119, 122, 123, 127, 128–130, 135, 137; 219/385, 386, 390, 391, 398, 402, 403, 406, 407, 420; 433/218, 222; 423/223; 164/35, 519–524, 695, 508, 61

[56] References Cited

U.S. PATENT DOCUMENTS

| | | | |
|---|---|---|---|
| 3,227,798 | 1/1966 | Delange et al. | 219/390 |
| 3,645,767 | 2/1972 | Taylor | 164/72 |
| 3,860,738 | 1/1975 | Hintenberger | 373/109 |
| 3,931,847 | 1/1976 | Terkelsen | 164/4 |
| 4,671,770 | 6/1987 | Bell et al. | 433/223 |
| 4,709,741 | 12/1987 | Nakamura | 164/35 |
| 5,432,319 | 7/1995 | Indig | 219/390 |
| 5,539,183 | 7/1996 | Beckley | 219/386 |
| 5,685,360 | 11/1997 | Bizzio | 164/508 |

*Primary Examiner*—Tu Ba Hoang

[57] ABSTRACT

A heating or preheating furnace for lining cylinders made of refractory material, where those cylinders are particularly designed to act as molds for the lost wax casting of precious metals, semiprecious metals, base metals or titanium or alloys thereof in order to obtain small items, dental prostheses, jewelry and costume jewelry items in general by precision casting. The furnace includes a bed, a hearth portion or base supporting the bed, an upper dome-shaped portion arranged to rest on the hearth portion to delimit a heating or firing chamber therewith, first driving means suitable for producing a relative motion between the dome-shaped portion and the hearth portion between a closed position, in which the dome-shaped portion rests on the hearth portion, and an open position, in which the dome-shaped portion is raised above the hearth portion, heating means carried by the dome-shaped portion, and a program control unit. The furnace also includes at least two work holding plates mounted for rotation in the hearth portion and a second driving means arranged to be controlled by the control unit and designed to cause each work holding plate to rotate about its own vertical axis.

17 Claims, 1 Drawing Sheet

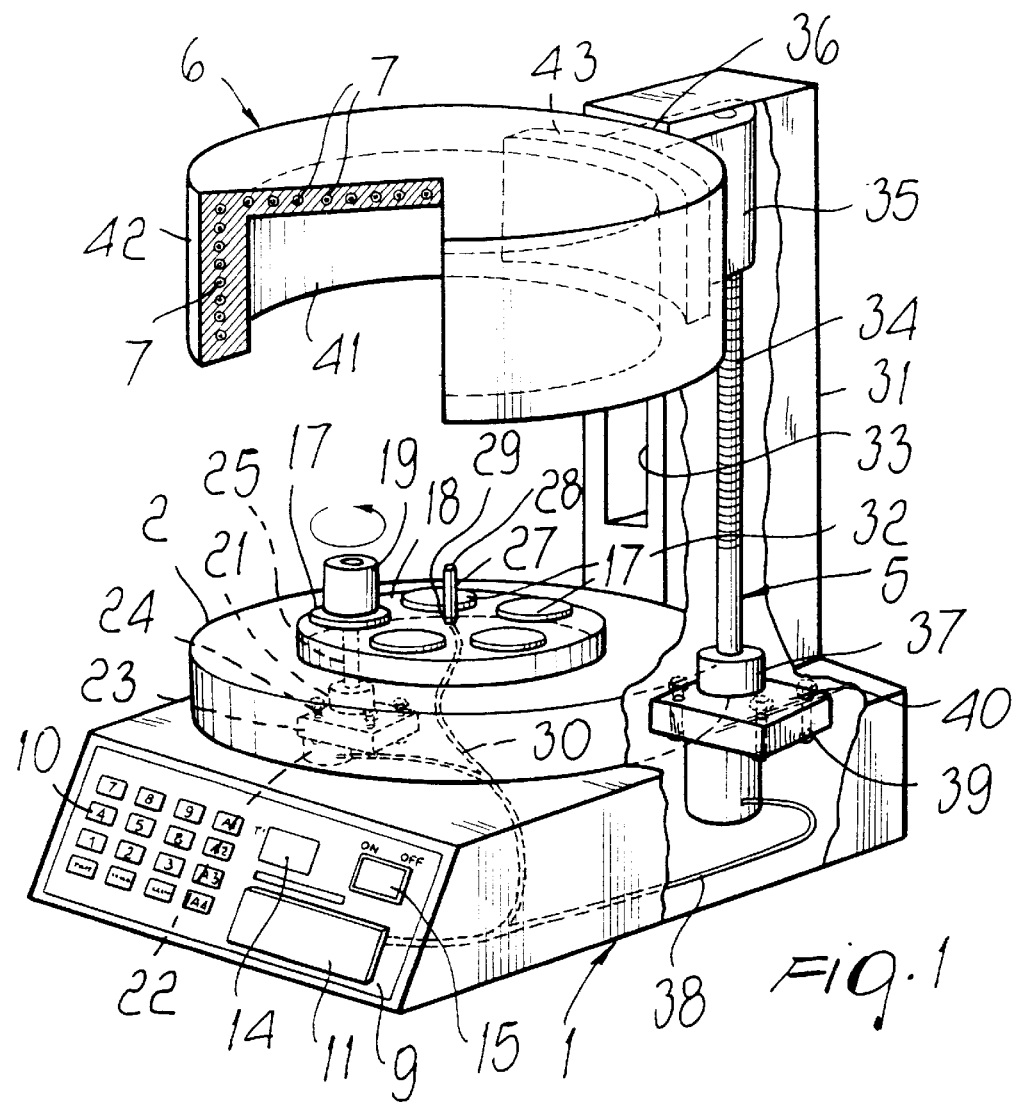
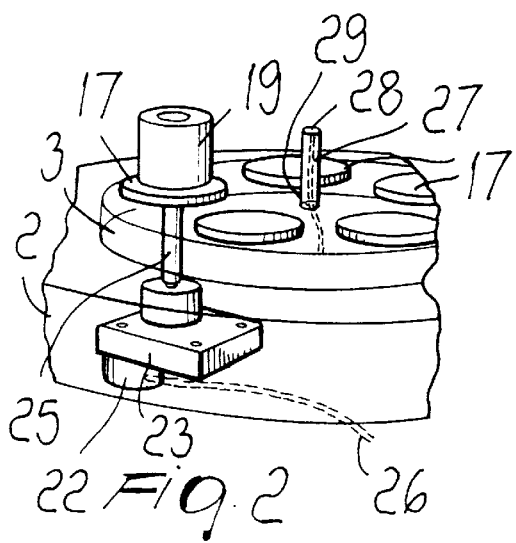
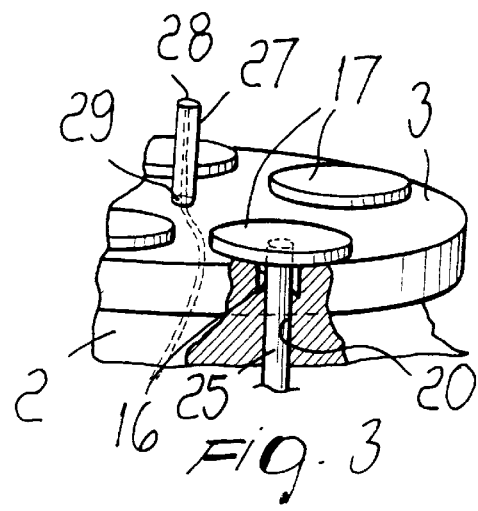

ELECTRIC HEATING OR PREHEATING FURNACE PARTICULARLY FOR LINING CYLINDERS AND/OR FOR FIRING METAL-CERAMIC

BACKGROUND OF THE INVENTION

The present invention relates to a heating or preheating furnace for so-called lining cylinders made of refractory material, particularly arranged to act as molds for the lost-wax casting of precious, semiprecious or base metals or titanium or alloys thereof to obtain small items, dental prostheses or jewelry and costume-jewelry items in general by precision casting.

As is known, for producing dental prostheses use is made of molds constituted by cylinders made of refractory material whose function is not merely that of containing but also adaptating (expanding) in order to make up for contraction of the cooling metal.

In order to ensure uniform expansion during baking or firing, the mold must be uniformly heat treated to prevent regions with a high thermal gradient from being formed which would give rise to differentiated or otherwise non-uniform expansion in the mold. The mold or lining must be treated at temperatures between 800° and 1000° C. within a suitable muffle furnace. It is important that said heating is uniform, otherwise the refractory material is subjected to changes in its behavior in terms of location and intensity of the expansions produced by temperature increase.

A drawback is the fact that conventional muffle furnaces designed to treat lining cylinders have an internal chamber delimited by walls, not all of which are provided with heating means. Accordingly, heat is radiated unevenly inside the chamber and this means that the refractory material of the lining cylinders does not undergo uniform heat treatment in all directions.

Furthermore, by arranging a plurality of cylinders inside the furnace, the cylinders near the walls provided with heating means form shadow zones for those located behind them, thereby producing a consequent uneven heat distribution, so that a lining cylinder can have regions exposed to different temperature levels.

SUMMARY OF THE INVENTION

The main object of the present invention is to provide a heating furnace for lining cylinders made of refractory material and for firing ceramics, particularly aesthetic dental ceramics on metal, which is arranged to eliminate or significantly reduce the drawbacks referred to above.

Another object of the present invention is to provide a heating or firing furnace which can operate also under controlled pressure, particularly at a pressure higher than the atmospheric pressure in order to obtain a much more compact ceramic material, thereby eliminating any air bubbles that might be formed in a conventional matrix obtained with conventional methods.

A further object of the present invention is to provide a furnace which is designed to obtain products of excellent quality without extending the treatment times and without altering the steps of treatment of said products.

These and other objects which will become more apparent hereinafter are achieved by a firing or baking furnace for lining cylinders made of refractory material, comprising:

a bed;

a lower hearth portion or base supported by said bed;

an upper dome-shaped portion arranged to rest on the hearth portion to delimit a heating chamber therewith;

first driving means suitable for producing a relative motion between said dome-shaped portion and said hearth-like portion between a closed position, in which said dome-shaped portion rests on said hearth-like portion, and an open position, in which said dome-shaped portion is raised above said hearth;

heating means carried by said dome-shaped portion;

a program control unit, at least two work holding plates mounted for rotation in said hearth-like portion, and second driving means arranged to be controlled by said control unit and designed to cause each work holding plate to rotate about its own vertical axis.

Advantageously, each work holding plate is seated in a respective recess formed in said hearth portion but is raised with respect thereto to ensure uniform heating both in the upper and lower part of the plate.

BRIEF DESCRIPTION OF THE DRAWINGS

Further aspects and advantages of the present invention will become more apparent from the following detailed description of a currently preferred embodiment thereof, given merely by way of a non-limiting example with reference to the accompanying drawing, wherein:

FIG. 1 is a slightly elevated perspective view with parts cut away of a muffle furnace according to the present invention;

FIG. 2 is a perspective view of the driving system of a work holding plate; and

FIG. 3 shows a detail of the hearth or base of the furnace of FIG. 1.

DESCRIPTION OF THE PREFERRED EMBODIMENTS

With reference to FIG. 1 of the drawing, a furnace according to the invention is formed by a supporting bed 1, on which a platform 2 made of refractory material is located which acts as a support for a hearth or fixed base 3 which is also made of refractory material and e.g. is integral with the platform 2; by an actuation device 5 for a dome or muffle 6 that can thus be moved between a lowered closed position in which it rests on the hearth 3 and a raised open position in which it is moved away from the hearth; and by a plurality of electrical resistors 7 which constitute the heating means and are supported by the muffle or dome 6.

The bed 1 can be a box-like container whose front face 9 acts as a console and is provided with a keyboard 10 for gaining access to an electronic control unit 11, a display 14 for displaying the results of programming and/or indications concerning the operation of the furnace 1 (e.g. temperature, time and rate of heating, etc.), and an on/off button 15 for starting/stopping the furnace.

The platform 2 is fixed in any suitable manner on the bed 1. The platform preferably has an external cylindrical shape and the hearth or base 3 can rest on it and is, for example cylindrical in shape.

The hearth 3 is formed with a plurality of circular through openings 16 which have multiple diameters and are uniformly angularly spaced from one another around the vertical axis of the hearth or base, as shown in FIG. 3. A respective plate 17 made of ceramic material is rotatably mounted in each one of the through openings 16 and is preferably raised or in relief with respect to the upper flat face 18 of the base 3. Each plate 17 is arranged to support a respective lining cylinder 19 to be subjected to heat treatment.

The platform 2 has, at each opening 16 of the base 3 and in alignment with it, a through hole 20 for the passage of a shaft 25 which is coaxial with a respective plate 17 and having one end thereof keyed to a plate and its other end kinematically connected to a respective reversible electric motor 21. The casing 22 of the electric motor 21 can be fixed, e.g. to a support plate 23 provided with holes 24 for respective fixing screws to the upper wall of the bed 1.

Each electric motor 21 is electrically connected to the power supply and control unit 11 by means of a cable 26. The operating speed of rotation of each plate 17 can be, for example, one revolution per minute.

An axial post 27 rises from the flat upper face 18 of the base or hearth 3, and a respective temperature sensor is applied at the top and base of this post. These sensors are designated by the reference numerals 28 and 29, respectively, and e.g. comprise thermocouples. Each sensor 28 and 29 is electrically connected to the electronic control unit 11 by means of a respective cable 30.

A box-like column 31 rises from the bed on the side opposite to the console 9 and has a longitudinal slot 33 at its face 32 directed toward the base 3.

A device for actuating the dome or muffle 6 is fitted inside the column 31 and can be constituted e.g. by a screw-and-nut transmission system, in which the screw is a threaded shaft 34 which longitudinally extends inside the column 31, whereas the nut 35 is rigidly connected to a cantilevered arm 36 which protrudes cantileverwise from the guiding slot 33 and supports, at its end, the dome or muffle 6, as further explained hereinafter.

The threaded shaft 34 can be actuated by a respective source of motion, e.g. an electric motor 37 which can be electrically connected to the control unit 11 by means of a cable 38. A support plate 39 can be fixed to the casing of the motor 37 formed with holes 40 for fixing screws to the bed 1.

The muffle or dome 6 preferably has a circular shape in a plan view, with an access lower opening 41 which is facing, in use, the hearth or base 3. The inside diameter of the opening 41 is slightly larger than the outer diameter of the hearth 3, so as to be arranged around the hearth in its closed position. The electric resistors 7 are controlled by the control unit 11 and are located in the cylindrical lateral wall 42 of the dome or muffle 6 so as to be arranged one over the other in spaced vertical alignment, so as to occupy substantially all or most of the height of the wall 42. The control unit 11 controls the differentiated operation of the electric resistors 7 depending upon the signals generated by the temperature sensors 28 and 29 which are supported at two different levels, approximately corresponding to the height of a cylinder 19, by the post 27. In other words, if the temperatures detected by the sensors 28 and 29 differ by more than a set threshold value, the control unit 11 switches on or off one or more resistors 7 in the wall 42 and/or in the top wall of the muffle, so as to obtain a uniform temperature in the whole region above, around and below the plates 17 and thus the lining cylinders.

Externally and at the arm 36, the wall 42 of the muffle 6 is engaged by a curved bracket 43 which is supported at the end of the arm 36 and is smaller in height than the dome or muffle 6. As can be easily understood, the threaded shaft 34 actuates the nut 35 so as to move the dome or muffle 6 between a raised open position for loading/unloading lining cylinders 19 and a lowered closed position around the hearth or base 3 for heat treating the lining cylinders 19.

The fact that the work holding plates 17 and thus the cylinders 19 are rotated in use results in shadow zones being eliminated even if the furnace is fully loaded. Since the plates 17 are raised with respect to the hearth or base 3, heat can be transmitted by radiation and/or convection also below each plate 17 made of ceramic material, but above the refractory base 3, thus ensuring uniform heating of the lining cylinders 19 from below as well.

The invention described above is susceptible to numerous modifications and variations within the protection scope defined by the appended claims.

Thus, for example, the various work holding plates 17 can be rotated by one source of motion by means of a planet-gear transmission or a chain drive.

Moreover, the device for lifting/lowering the dome or muffle 6 can also be actuated manually, e.g. by means of a pedal-driven lever system.

At the dome or hearth it is possible to provide an inlet for air or another gas or mixture of gases under pressure, fed from a suitable source (not shown in the drawings) and connected to the inlet in any suitable manner in order to perform heating or firing under a controlled pressure higher than the atmospheric pressure in order to compress the ceramic material and make it much more compact, since any air bubbles, that might be present in a matrix obtained by conventional methods, are thus eliminated from it. In this case, suitable sealing gaskets are provided along the lower edge of the dome and optionally in the hearth at each rotating plate 17.

The control unit 11 can store a multiplicity of treatment cycles, thereby making it possible to program the temperature, the heating rate, the retention time at the treatment temperature, etc.

The dome or muffle 6 can have an opening for connection to a fume aspirator and can be provided with any suitable safety device which is arranged to prevent furnace 1 from being closed or operated when the muffle is open.

What is claimed is:

1. A heating or preheating furnace for lining cylinders made of refractory material comprising:
    a bed;
    a hearth portion supported by said bed;
    an upper dome-shaped portion arranged to rest on said hearth portion to delimit a heating/firing chamber therewith;
    first driving means suitable for producing relative motion between said dome-shaped portion and said hearth portion, where said relative motion varies between a closed position, in which said dome-shaped portion rests on said hearth portion, and an open position, in which said dome portion is raised above said hearth portion;
    heating means carried by said dome-shaped portion; and
    a program control unit,
    at least two work holding plates mounted for rotation on said hearth portion, and second driving means arranged to be controlled by said control unit and designed to cause each work holding plate to rotate about its own vertical axis.

2. The furnace according to claim 1, wherein each work holding plate comprises a lower face and an upper face and is raised with respect to said hearth portion to ensure uniform heating of said lower face and said upper face.

3. The furnace according to claim 1, wherein said hearth portion has a through opening for receiving a respective work holding plate.

4. The furnace according to claim 3 comprising a rotary supporting shaft for each work holding plate, said shaft extending through said hearth portion and said bed.

5. The furnace according to claim 1, wherein said second driving means comprises a source of motion which is located in said bed and is operatively connected to each work holding plate.

6. The furnace according to claim 1, wherein said second driving means comprises one source of motion which is operatively connected to each work holding plate.

7. The furnace according to claim 1, wherein said bed includes a box-like casing supporting a platform, and a plurality of through openings in said hearth portion.

8. The furnace according to claim 1, comprising a sensor support rising from said hearth portion and at least one upper temperature sensor supported at the top of said support and at least one lower temperature sensor supported at the same level as said hearth portion, both said sensors being electrically connected to said control unit.

9. The furnace according to claim 8, wherein each temperature sensor comprises at least one thermocouple.

10. The furnace according to claim 8, further comprising an axial post extending from said hearth portion, the height of said axial post being approximately equal to the height of a work supported by its respective work holding plate.

11. The furnace according to claim 10, wherein said heating means extends around said heating/firing chamber along a peripheral zone whose width is substantially equal to the height of the work or works held by each work holding plate.

12. The furnace according to claim 11, wherein said heating means comprises a plurality of heating elements arranged one above the other in said peripheral zone, said heating means being controlled by said control unit, so as to differentially control the temperature at multiple levels in said heating/firing chamber.

13. The furnace according to claim 12, wherein said heating means comprises at least one heating element at the top of said heating/firing chamber.

14. The furnace according to claim 13, wherein said heating means are controlled in response to signals from said upper and lower temperature sensors.

15. The furnace according to claim 1, wherein said first driving means for said dome-shaped portion comprises a linear actor driven on command.

16. The furnace according to claim 1, comprising a pressurized fluid source and connection means between said source and said heating/firing chamber to pressurize said heating/firing chamber.

17. The furnace according to claim 16, comprising sealing means between said dome-shaped portion and said hearth portion.

* * * * *